United States Patent [19]

Huth

[11] Patent Number: 5,210,274

[45] Date of Patent: May 11, 1993

[54] ETHYLENICALLY UNSATURATED, FLORINE-CONTAINING URETHANE DERIVATIVES AND PROCESS FOR THEIR PREPARATION

[75] Inventor: Hans-Ullrich Huth, Egelsbach, Fed. Rep. of Germany

[73] Assignee: Hoechst AG, Fed. Rep. of Germany

[21] Appl. No.: 661,052

[22] Filed: Feb. 25, 1991

[30] Foreign Application Priority Data

Feb. 27, 1990 [DE]  Fed. Rep. of Germany ....... 4006097

[51] Int. Cl.$^5$ .............................................. C07C 271/14
[52] U.S. Cl. ........................................ 560/26; 560/25; 560/115; 560/158; 560/159; 560/160; 560/167; 560/24
[58] Field of Search ............... 560/167, 163, 162, 160, 560/158, 159, 167, 115, 24, 25, 26

[56] References Cited

U.S. PATENT DOCUMENTS

| | | | |
|---|---|---|---|
| 4,584,143 | 4/1986 | Falle | 558/240 |
| 4,687,872 | 8/1987 | Grate et al. | 560/25 |
| 4,920,190 | 4/1990 | Lina et al. | 526/288 |

FOREIGN PATENT DOCUMENTS 625613  6/1963  Belgium .

Primary Examiner—Joseph L. Schofer
Assistant Examiner—M. Nagumo
Attorney, Agent, or Firm—Bierman and Muserlian

[57] ABSTRACT

Ethylenically unsaturated, fluorine-containing urethane derivatives (see Formula I) whose urethane group is substituted on its carboxyl radical by a fluorinated organic radical and on its nitrogen atom by an unfluorinated, ethylenically unsaturated organic radical. Their preparation can be carried out by reacting ethylenically unsaturated, unfluorinated isocyanates with fluorinated organic hydroxyl compounds in bulk in the absence of water or advantageously in inert organic solvents or in ethylenically unsaturated monomers capable of polymerization which behave inertly under the reaction conditions, it being possible to obtain the urethane derivatives directly in liquid or highly viscous or waxy or solid or crystalline form.

Urethane derivatives prepared according to the invention are usually readily to very readily soluble in standard nonaqueous, nonpolar inert organic solvents or in various monomers capable of copolymerization. They can be polymerized or copolymerized in a free-radical way and used to prepare polymers or copolymers.

5 Claims, No Drawings

ETHYLENICALLY UNSATURATED, FLORINE-CONTAINING URETHANE DERIVATIVES AND PROCESS FOR THEIR PREPARATION

DESCRIPTION

The invention relates to ethylenically unsaturated, fluorine-containing urethane derivatives whose urethane group is substituted on its carboxyl radical by a fluorinated alkyl, alkoxyalkyl, aryloxyalkyl, alkylaryloxyalkyl or arylalkoxyalkyl radical and on its nitrogen atom by an unfluorinated, ethylenically unsaturated organic radical and which can be polymerized or copolymerized, inter alia, in a free-radical way and also a process for their preparation.

European Patent 24 908 discloses the preparation of ethylenically unsaturated, fluorine-containing urethanes whose urethane group may have a fluoroalkyl radical on the nitrogen atom. Polymers made from these urethanes are said to be soluble in nontoxic solvents and usable as a dirt-repellent finish having good adhesion to textiles and leathers and a high softening point.

U.S. Pat. No. 4,540,805 discloses the preparation of ethylenically unsaturated, fluorine-containing urethanes whose urethane group is substituted on the carboxyl radical by fluorinated thioether radicals. The compounds can be converted, by bulk, solution or emulsion polymerization, into polymers which are said to be usable, inter alia, for water- and oil-repellent coating of textiles.

European Patent 225 826 discloses the preparation of ethylenically unsaturated, fluorine-containing bisurethanes which can be obtained by stepwise reaction of, firstly, an isocyanate group of toluylene diisocyanate with a fluoroalkanol and then of the other isocyanate group with a hydroxyalkyl (meth)acrylate. The process has the disadvantage that in up to 40% of the toluylene diisocyanate, both the isocyanate groups already react with the fluoroalkanol in the first stage, and this results in considerable losses and necessitates expensive separation operations. Homopolymers and copolymers of the fluorine-containing bisurethanes prepared by solution polymerization are said to be usable for the preparation of water- and oil-repellent coatings on textiles and leather.

As has been shown in practice, the ethylenically unsaturated, fluorine-containing urethanes hitherto disclosed have a number of disadvantages such as, for example, starting components which are difficult and expensive to obtain, unsatisfactory yields in the preparation processes, the need for complex purification operations in order to eliminate byproducts, unsatisfactory solubilities in solvents when the monomers are used further as intermediates, unsatisfactory homopolymerization and/or copolymerization behavior and also an inadequate property spectrum of polymers and/or copolymers.

The object of the invention is therefore to overcome the abovementioned difficulties and to provide monomeric, ethylenically unsaturated, fluorine-containing urethanes which are simple and economic to prepare and whose property spectrum makes possible a broad and problem-free range of applications.

Surprisingly, ethylenically unsaturated, fluorine-containing urethane derivatives whose urethane group is substituted on its carboxyl radical by a fluorinated organic radical and on its nitrogen atom by an unfluorinated, ethylenically unsaturated organic radical, and furthermore processes for their preparation have now been found. The urethane derivatives according to the invention are liquid or solid under normal conditions, have good solubility in the organic solvents normally needed for their further use and can advantageously and versatilely be used, for example, for the preparation of polymers or copolymers.

The invention therefore relates to ethylenically unsaturated, fluorine-containing urethane derivatives of the Formula I, $$\underset{R^2}{\overset{R^1}{\diagdown}}C=C-A-N-C-O-(CH_2)_x-R^4 \quad \text{(I)}$$
$$\qquad\qquad \underset{R^3}{|} \ \underset{H}{|} \ \underset{O}{\|}$$

in which $R^1$ to $R^4$, A and the numerical index x have the following meanings:

$R^1$, $R^2$, and $R^3$, which may be identical or different, are H, —$CH_3$, preferably $R^1$ and $R^2$ are H and $R^3$ is —$CH_3$, x is 1 or 2

A is —$(CH_2)_y$—, y is 1 to 6, tert-butylphenylene —[$C_6$-$H_3$—$C(CH_3)_3$]— or —$C_6H_4C(CH_3)_2$— or $$-(CH_2)_k-(C)_m-(Z-CH_2-CH)_n-(O-C-N-B)_p-,$$
$$\qquad\quad \underset{O}{\|}\qquad\qquad \underset{R^5}{|}\qquad \underset{O}{\|}\ \underset{H}{|}$$

where
Z is oxygen or NH, preferably oxygen,
$R^5$ is H, —$CH_3$, —$C_2H_5$,
B is ($C_6$-$C_{16}$)arylene which may contain ($C_1$-$C_{10}$)alkyl radicals, preferably phenylene, toluylene, tert-butylphenylene, naphthylene, ($C_2$-$C_{12}$)alkylene or ($C_6$-$C_{10}$)-cycloalkylene,
k, m, p are 0 or 1, preferably m is 1,
n is 1 to 5, preferably 1,
$R^4$ is —$(C_2F_4)_qH$, —$(CF_2)_rH$, —$(C_rF_{2r+1})$, —$C_rF_{2r}$—O—$R^6$,
q is 1 to 6, preferably 1 to 3,
r is 1 to 9, preferably 1 to 6,
$R^6$ is ($C_1$-$C_{12}$)alkyl which may be partially or fully substituted by fluorine atoms, or is ($C_6$-$C_{12}$)aryl or ($C_7$-$C_{12}$)alkaryl which may be partially or fully substituted by fluorine atoms.

Particularly preferred urethane derivatives are those in which, in Formula I, $R^1$ and $R^2$ are H, $R^3$ is H or —$CH_3$, or $R^1$ and $R^3$ are H, $R^2$ is —$CH_3$ and Z is oxygen.

The invention furthermore relates to a process for the preparation of ethylenically unsaturated, fluorine-containing urethane derivatives of the Formula I, $$\underset{R^2}{\overset{R^1}{\diagdown}}C=C-A-N-C-O-(CH_2)_x-R^4 \quad \text{(I)}$$
$$\qquad\qquad \underset{R^3}{|} \ \underset{H}{|} \ \underset{O}{\|}$$

in which $R^1$ to $R^4$, A and x have the abovementioned meanings, by reacting isocyanates with organic hydroxyl compounds, which process comprises reacting isocyanates of the Formula II,

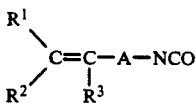
(II)

in which $R^1$ to $R^3$ and A have the meaning as in Formula I, with equimolar amounts of hydroxyl compounds of the Formula III,

(III)

in which $R^4$ and x have the meaning as in Formula I.

Preferred starting components of the Formula II are, for example, the following ethylenically unsaturated compounds having a terminal isocyanate group:

Isocyanatoethyl acrylate, isocyanatoethyl methacrylate, isocyanatopropyl methacrylate, isocyanatopropyl acrylate, isocyanatoethyl crotonate, o-isopropenyl-α,α-dimethylbenzyl isocyanate, m-isopropenyl-α,α-dimethylbenzyl isocyanate, p-isopropenyl-α,α-dimethylbenzyl isocyanate, vinyl isocyanate, propenyl isocyanate, 2-methacryloyloxyethyl isocyanatotoluylcarbamate, 2-acryloyloxyethyl isocyanatotoluylcarbamate, 3-methacryloyloxypropyl isocyanatotoluylcarbamate, 3-acryloyloxypropyl isocyanatotoluylcarbamate, 2-crotonoyloxyethyl isocyanatotoluylcarbamate, 2-methacryloyloxyethyl 6-isocyanatohexylcarbamate, 2-acryloyloxyethyl 6-isocyanatohexylcarbamate, 3-methacryloyloxypropyl 6-isocyanatohexylcarbamate, 3-acryloyloxypropy6-isocyanatohexylcarbamate,2-crotonoyloxyethyl 6-isocyanatohexylcarbamate, 2-methacryloyloxyethyl (5-isocyanato-1,3,3-trimethylcyclohexyl)methylcarbamate, 2-acryloyloxyethyl (5-isocyanato-1,3,3-trimethylcyclohexyl)methylcarbamate, 3-methacryloyloxypropyl (5-isocyanato-1,3,3-trimethylcyclohexyl)methylcarbamate, 3-acryloyloxypropyl (5-isocyanato-1,3,3-trimethylcyclohexyl)methylcarbamate, 2-crotonoyloxyethyl (5-isocyanato-1,3,3-trimethylcyclohexyl)methylcarbamate, 2-methacryloyloxyethyl (3-isocyanatomethyl-3,5,5-trimethylcyclohexyl)carbamate, 2-acryloyloxyethyl (3-isocyanatomethyl-3,5,5-trimethylcyclohexyl)carbamate, 3-methacryloyloxypropyl (3-isocyanatomethyl-3,5,5-trimethylcyclohexyl)carbamate, 3-acryloyloxypropyl (3-isocyanatomethyl-3,5,5-trimethylcyclohexyl)carbamate, 2-crotonoyloxyethyl (3-isocyanatomethyl-3,5,5-trimethylcyclohexyl)carbamate.

The compounds of Formula II are known per se and can be prepared by known methods.

Suitable hydroxyl compounds of the Formula III are, for example, preferably all the straight-chain or branched fluoroalkanols, fluoroalkoxy- or fluorophenoxyfluoroalkanols, in particular, for example, 2,2,3,3-tetrafluoro-1-propanol,1,1,1,3,3,3-hexafluoro-2-propano,2,2,3,4,4,4-hexafluoro-1-butanol, 2,3,3,4,4,5,5,5-octafluoro-1-pentanol, 2-perfluorohexylethanol and 2-perfluorooctylethanol.

The process is preferably carried out according to the invention by carrying out the reactions in bulk or in inert organic solvents or, optionally, in ethylenically unsaturated monomers capable of copolymerization which behave inertly under the reaction conditions (reactive diluents) in the absence of water, preferably at temperatures between 0° C. and 100° C., in particular between 0° and 80° C.

Used as inert organic solvents are the inert solvents normally used in organic syntheses with isocyanates in an anhydrous medium provided they are able to fulfil, inter alia the requirements relating to solvent action and boiling range.

Preferred inert solvents are, for example, toluene, tetrahydrofuran (THF), ethyl acetate and hexane.

In some cases so-called reactive diluents may also be advantageous as solvents, these being monomers which are capable of copolymerization and which behave inertly under the synthesis conditions of the formation of urethane groups according to the invention but can be polymerize later with the unsaturated urethane derivatives of the Formula I under suitable polymerization conditions. Preferred inert reactive diluents are accordingly, for example, (meth)acrylates, styrene and vinylesters, in which case the work is carried out below the saturation concentration of the reactants if they are used.

Optionally, a catalyst is also used in the isocyanate addition according to the invention, inter alia, to be able to keep the reaction temperature as low as possible, and this may be advantageous, in particular if reactive diluents are used. Preferred catalysts are organic tin compounds which are preferably used in solution in an inert organic solvent.

Particularly preferred is the use of dibutyltin dilaurate, optionally in combination with tert-butylpyrocatechol, and furthermore, for example, of tert-amines such as, for example, dimethylpiperazine, 1,4-diazobicyclo[2.2.2] octane.

The compounds of the Formula I prepared according to the invention are in most cases obtained directly in liquid or highly-viscous or waxy or solid or crystalline form and may be used further, optionally after eliminating concomitantly used solvents, in general without further purification and drying as intermediates in bulk or, optionally, dissolved in organic solvents or emulsified or dispersed in water.

Of course, the crude reaction products produced in the synthesis process according to the invention can also be purified by standard methods such as, for example, elution, recrystallization, reprecipitation and/or distillation of volatile components, optionally using reduced pressure and optionally concomitantly using standard polymerization inhibitors, and also optionally using protective gas, and the compounds of Formula I obtained in chemically pure form.

The fluorine-containing compounds of the Formula I are capable of polymerization and copolymerization. In general they are readily to very readily soluble in standard nonaqueous, nonpolar inert organic solvents and also in the so-called reactive diluents already mentioned above and are suitable, in particular, as monomers or co-monomers for polymerizations. In this connection it was found, surprisingly, that polymers prepared by free-radical-initiated emulsion or suspension polymerization from monomers of Formula I and also in particular, copolymers based on ethylenically unsaturated monomers which contain at least 0.1% by weight of monomer units of fluorine-containing urethane derivatives of Formula I of the present invention have unexpectedly advantageous properties.

These copolymers, their range of applications, in particular in the form of aqueous copolymer dispersions, and also their preparation using monomeric fluorine-containing urethane derivatives of the Formula I of the present invention as starting products are, inter alia, the subject of the U.S. patent application Ser. No.

661,053 pending filed on the same date which is included herein by reference.

The invention is explained in greater detail by the examples below without thereby limiting it.

EXAMPLES 1-5

Preparation of ethylenically unsaturated, fluorine-containing urethane derivatives of the Formula I by reacting equimolar amounts of starting components of the Formulae II and III in bulk

Example 1

92 g of the Formula III compound 2,2,3,3-tetrafluoro-1-propanol (0.69 mol) and 2 drops of dibutyltin dilaurate are introduced into a 0.25 l four-necked flask fitted with stirrer, thermometer, dropping funnel and reflux condenser with $CaCl_2$ end tube and heated to 50° C. 108.08 g of the Formula II isocyanate isocyanatoethyl methacrylate (0.69 mol) are then added dropwise to this mixture while stirring in the course of 45 minutes, during which process the internal temperature of the mixture rises to 58° C. Stirring of the mixture is then continued at 80° C. until the NCO band in the IR spectrum of the reaction mixture has disappeared (time approximately 2 days). When the mixture is subsequently cooled, the contents of the flask crystallize completely. They are comminuted in a mortar, washed with a total of 88 ml of cyclohexane and dried under vacuum. 189.8 g of the corresponding ethylenically unsaturated, fluorine-containing urethane derivative of Formula I is obtained in brightly colored solid form (yield=94.9% of theory), with a melting point Mp. (capillary method) of 44° C.

Example 2

Example 1 is repeated with replacement of the reactants with the modification that 0.69 mol of the Formula III compound 2,2,3,4,4,4-hexafluoro-1-butanol and 0.69 mol of the Formula II isocyanate $$H_2C=\overset{CH_3}{\underset{|}{C}}-\overset{O}{\underset{\|}{C}}-O-CH_2-CH_2-NCO$$

are used reactants. Cyclohexane washing is not employed and virtually 100% yield of the corresponding ethylenically unsaturated, fluorine-containing urethane derivative of the Formula I is obtained in liquid, colorless form. The boiling point at normal pressure is at over 160° C., with decomposition. The compound has the formula $H_2C=C-(CH_3)-COOCH_2-CH_2NH-COOCH-CF_2-CHFCF_3$.

Example 3

Example 1 is repeated with reactant replacement with the modification that 0.69 mol of the Formula III compound 1,1,1,3,3,3-hexafluoro-2-propanol and 0.69 mol of the Formula II isocyanate $$CH_2=\overset{CH_3}{\underset{|}{C}}-\overset{O}{\underset{\|}{C}}-O-CH_2-CH_2-NCO$$

are used as reactants. The corresponding ethylenically unsaturated, fluorine-containing urethane derivative of Formula I is obtained after carrying out cyclohexane washing in brightly colored solid form with 95% yield. The melting point Mp. (capillary method) is 55° C.

Example 4

Example 1 is repeated with reactant replacement with the modification that 0.69 mol of the Formula III compound 2,2,3,3-tetrafluoro-1-propanol and 0.69 mol of the Formula II isocyanate $$CH_2=\overset{CH_3}{\underset{|}{C}}-\underset{\phantom{xx}}{\text{C}_6H_4}-\overset{CH_3}{\underset{\underset{CH_3}{|}}{\overset{|}{C}}}-NCO$$

are used as reactants. The corresponding ethylenically unsaturated, fluorine-containing urethane derivative of the Formula I is obtained after carrying out cyclohexane washing in brightly colored solid form with 96.5% yield. The melting point Mp. (capillary method) is 55°–58° C.

Example 5

Example 1 is repeated with reactant replacement with the modification that 0.69 mol of the Formula III compound 2,2,3,4,4,4-hexafluoro-1-butanol and 0.69 mol of the Formula II isocyanate $$CH_2=\overset{CH_3}{\underset{|}{C}}-\overset{O}{\underset{\|}{C}}-O-CH_2-CH_2-O-\overset{O}{\underset{\|}{C}}-NH-\underset{\phantom{xx}}{\text{C}_6H_3(CH_3)}-NCO$$

are used as reactants. The corresponding ethylenically unsaturated, fluorine-containing urethane derivative of the Formula I is obtained after carrying out cyclohexane washing in brightly colored solid form with 95% yield. The melting point Mp. (capillary method) is 84°–87° C.

I claim:

1. An ethylenically unsaturated, fluorine-containing urethane derivative of the Formula I, $$\underset{R^2}{\overset{R^1}{\diagdown}}C=\underset{R^3}{\overset{\phantom{x}}{C}}-A-\underset{H}{\overset{\phantom{x}}{N}}-\underset{O}{\overset{\|}{C}}-O-(CH_2)_x-R^4 \qquad (I)$$

in which $R^1$ to $R^4$, A and the numerical index x have the following meanings:

$R^1$, $R^2$ and $R^3$, which may be identical or different, are H, $-CH_3$, x is 1 or 2

A is $-(CH_2)_y-$, y is 1 to 6, tert-butylphenylene—$[C_6H_3-C(CH_3)_3]-$ or $-C_6H_4C(CH_3)_2-$ or $$-(CH_2)_k-\underset{O}{\overset{\|}{(C)}}_m-(Z-CH_2-\underset{R^5}{\overset{|}{CH}})_n-(O-\underset{O}{\overset{\|}{C}}-\underset{H}{\overset{|}{N}}-B)_p-$$

where

Z is oxygen or NH, $R^5$ is H, $-CH_3$, $-C_2H_5$,

B is ($C_6$–$C_{16}$)arylene which may contain ($C_1$–$C_{10}$)alkyl radicals, ($C_2$–$C_{12}$)alkylen or ($C_6$–$C_{10}$)cycloalkylene, k, m, p are 0 or 1, n is 1 to 5,
$R^4$ is —$(C_2F_4)_qH$, —$(CF_2)_rH$, —$C_rF_{2r}$—O—$R^6$,
q is 1 to 6,
r is 1 to 9,
$R^5$ is ($C_1$–$C_{12}$)alkyl which may be partially or fully substituted by fluorine atoms, or is ($C_6$–$C_{12}$)aryl or ($C_7$–$C_{12}$)alkaryl which may be partially or fully substituted by 2. A urethane derivative as claimed in claim 1, wherein, in Formula I, $R^1$ and $R^2$ are H, $R^3$ is H or —$CH_3$, or $R^1$ and $R^3$ are H, $R^2$ is —$CH_3$ and Z is oxygen.

3. A process for the preparation of ethylenically unsaturated, fluorine-containing urethane derivatives of the Formula I as claimed in claim 1

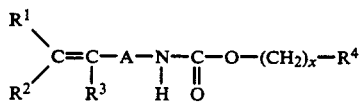

in which $R^1$ to $R^4$, A and x have the meaning as in Formula I in claim 1, by reacting isocyanates with organic hydroxyl compounds, which process comprises reacting isocyanates of the Formula II,

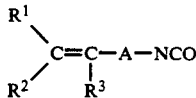

in which $R^1$ to $R^3$ and A have the meaning as in Formula I, with equimolar amounts of hydroxyl compounds of the Formula III, $R^4$—$(CH_2)_x$—OH    (III)

in which $R^4$ and x have the meaning as in Formula I.

4. The process as claimed in claim 3, wherein the reaction is carried out in bulk or in inert organic solvents or in ethylenically unsaturated monomers capable of copolymerization which behave inertly under the reaction conditions, in the absence of water.

5. A process for the preparation of an ethylenically unsaturated, fluorine containing urethane derivative comprising reacting an isocyanate of the formula

wherein $R_1$, $R_2$ and $R_3$ are individually selected from the group consisting of hydrogen and methyl and A is selected from the group consisting of —$(CH_2)_y$—, tert-butylphenylene, —$C_6H_4$—$C(CH_3)_2$— and —$(CH_2)_b$—(—CO)$_m$—(Z—$CH_2CHR^5$)$_n$—(O—CO—NH—B)$_p$—, y is 1 to 6, b, m and p are 0 to 1, n is 1 to 5, Z is —O— or —NH—, $R^5$ is —H, —$CH_3$, or —$C_2H_5$, and B is ($C_6$ to $C_{16}$) arylene optionally substituted with alkyl of 1 to 10 carbon atoms with an equimolar amount of an alcohol selected from the group consisting of 2,2,3,3-tetrafluoro-1-propanol, 1,1,1,3,3,3-hexafluoro-2-propanol, 2,2,3,4,4,4-hexafluoro-1-butanol, 2,3,3,4,4,5,5,5-octafluoro-1-pentanol, 2-perfluorohexylethanol and 2-perfluorooctylethanol.

* * * * *